United States Patent [19]

Hellerbach et al.

[11] 4,155,913

[45] May 22, 1979

[54] THIENOTRIAZOLODIAZEPINE DERIVATIVES

[75] Inventors: Joseph Hellerbach, Basel; Paul Zeller, Allschwil, both of Switzerland; Dieter Binder; Otto Hromatka, both of Vienna, Austria

[73] Assignee: Hoffmann-La Roche Inc., Nutley, N.J.

[21] Appl. No.: 842,028

[22] Filed: Oct. 14, 1977

Related U.S. Application Data

[63] Continuation of Ser. No. 686,761, May 17, 1976, abandoned, which is a continuation of Ser. No. 438,982, Feb. 4, 1974, abandoned.

[30] Foreign Application Priority Data

Feb. 8, 1973 [CH] Switzerland ................. 1799/73
Jan. 11, 1974 [CH] Switzerland ................. 354/74

[51] Int. Cl.$^2$ ............................. C07D 495/14
[52] U.S. Cl. .................. 260/308 R; 260/293.3 B; 260/244.4; 546/276; 546/284; 546/193; 260/329 F; 260/332.2 R; 260/332.3 R; 424/263; 424/269; 260/243.3; 546/210; 546/213; 544/131; 544/132; 544/366; 544/146; 544/379
[58] Field of Search ....................... 260/308 R

[56] References Cited

U.S. PATENT DOCUMENTS

| | | | |
|---|---|---|---|
| 3,734,922 | 5/1973 | Hester | 260/308 R |
| 3,759,943 | 9/1973 | Hester | 260/308 R |
| 3,842,090 | 10/1974 | Gall et al. | 260/308 R |
| 3,904,641 | 9/1975 | Nakanishi et al. | 260/308 R |

FOREIGN PATENT DOCUMENTS

| | | | |
|---|---|---|---|
| 2229845 | 12/1972 | Fed. Rep. of Germany | 260/308 R |
| 7015430 | 4/1971 | Netherlands | 260/308 R |

*Primary Examiner*—Alton D. Rollins
*Attorney, Agent, or Firm*—Jon S. Saxe; Bernard S. Leon; Frank P. Hoffman

[57] ABSTRACT

Novel thienotriazolodiazepine derivatives and processes for their preparation are described. These compounds are useful as anticonvulsants, muscle-relaxants and sedatives.

2 Claims, No Drawings

THIENOTRIAZOLODIAZEPINE DERIVATIVES

This is a continuation, of application Ser. No. 686,761 filed May 17, 1976, now abandoned which is the continuation of Ser. No. 438,982, filed Feb. 4, 1974, now abandoned.

DESCRIPTION OF THE INVENTION

The present invention relates to novel chemical compounds and to processes for the preparation thereof, said compounds having valuable therapeutic properties. More particularly, the present invention is concerned with new thienotriazolodiazepine derivatives of the general formula

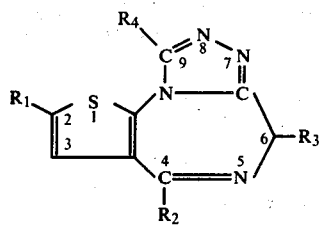

I and of the general formula

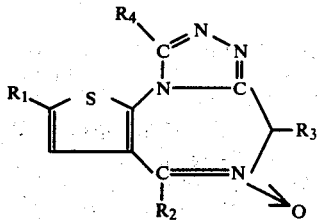

II wherein $R_1$ is selected from the group consisting of hydrogen, halogen, nitro, lower alkyl, amino and lower alkanoyl;

$R_2$ is selected from the group consisting of

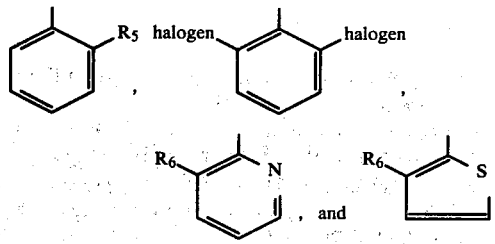

$R_3$ signifies hydrogen, hydroxy, lower alkoxy carbonyl or lower alkanoyloxy; $R_4$ signifies hydrogen, lower alkyl, lower alkanoyl, hydroxy lower alkyl, mercapto lower alkyl, lower alkoxy carbonyl, aminocarbonyl, halo lower alkyl, lower alkoxy lower alkyl, lower alkylthio lower alkyl, aralkoxy lower alkyl, cyano lower alkyl, lower alkoxycarbonyl lower alkyl, lower alkoxy carbonylamino lower alkyl, lower alkylcarbonyloxy lower alkyl, aminocarbonyloxy lower alkyl, di-lower alkylaminocarbonyloxy lower alkyl, cyano or a group of the formula-lower alkyl-Z,-COO-lower alkyl-Z or -CO-NH-lower alkyl-Z in which Z signifies the grouping -N($R_7$)($R_8$) wherein $R_7$ and $R_8$ are each independently hydrogen, lower alkyl or hydroxy-lower alkyl or $R_7$ and $R_8$ taken together with the nitrogen atom to which they are attached represent a 5 or 6-membered saturated heterocyclic ring which may contain a further nitrogen atom or an oxygen atom; $R_5$ signifies hydrogen, halogen, nitro or trifluoromethyl; $R_6$ signifies hydrogen, halogen or lower alkyl;

and the pharmaceutically acceptable acid addition salts thereof.

As used herein either alone or in combination the term "lower alkyl" comprehends straight or branched chain hydrocarbon groups having from 1 to 4 carbon atoms such as, for example, methyl, ethyl, propyl, isopropyl, tertiary butyl and the like. The term "halogen" represents all four forms thereof, i.e., fluorine, chlorine bromine and iodine, unless expressly indicated otherwise. The term "lower alkoxy" designates straight or branched chain, saturated hydrocarbonoxy groups containing from 1 to 4 carbon atoms, such as methoxy, ethoxy, propoxy and the like. The term "lower alkanoyl" denotes the acyl residue derived from a straight or branched chain saturated aliphatic carboxylic acid containing from 1 to 4 carbon atoms, such as, for example, formyl, acetyl, propionyl and the like. The term "lower alkanoyloxy" denotes a lower alkanoyl residue having a substituted oxygen function such as, for example acetoxy, propionyloxy and the like. The term "aralkoxy lower alkyl" denotes a lower alkoxy lower alkyl group in which a hydrogen atom is replaced by an optionally substituted phenyl residue. Examples of the pyridyl and thieno groups which may define the $R_2$ substituent and which may be substituted adjacent to the position linking said groups to the diazepine ring are 3-methyl-2-pyridyl and 3-chloro-2-thienyl. A preferred class of compounds falling within the scope of formulae I and II above are those wherein $R_1$ signifies a halogen atom, preferably chlorine and $R_2$ signifies orthohalophenyl 2,6-diahalophenyl or 2-pyridyl, ie. compounds of the formula

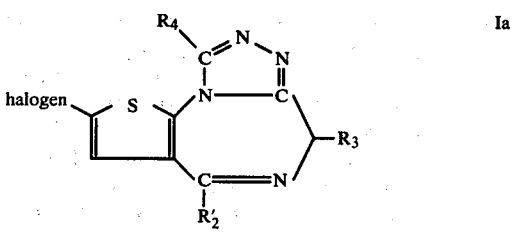

Ia and of the formula

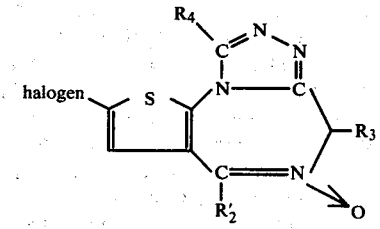

IIa wherein $R_3$ and $R_4$ are as described above and $R_2'$ signifies orthohalophenyl, 2,6-dihalophenyl or 2-pyridyl and the pharmaceutically acceptable acid addition salts thereof.

When the $R_2$ substituent signifies an orthohalophenyl group, the orthofluorophenyl and orthochlorophenyl groups are preferred. When the $R_2$ substituent signifies 2,6-dihalophenyl, the 2-halogen atoms are preferably identical and most preferably are fluorine atoms. In another preferred aspect the $R_3$ group is either hydrogen or hydroxy with hydrogen being the most preferred. The $R_4$ substituent is preferably a lower alkyl group, a hydroxy lower alkyl group or an amino lower alkyl group. When the $R_4$ substituent represents a lower alkyl group methyl is preferred. When the $R_4$ substituent represents hydroxy lower alkyl, hydroxy methyl and 2-hydroxy ethyl are preferred, while when the $R_4$ substituent represents amino lower alkyl aminomethyl or 2-aminoethyl are preferred.

Most preferred of the compounds of formula I above is 2-chloro-4-orthochlorophenyl-9-methyl-6H-thieno[3,2-f]-s-triazolo [4,3-a][1,4]diazepine.

The novel compounds of formulae I and II above can be prepared following a variety of synthetic routes.

A. In one such process the compounds of formulae I and II above can be prepared via the cyclization of a compound of the general formula

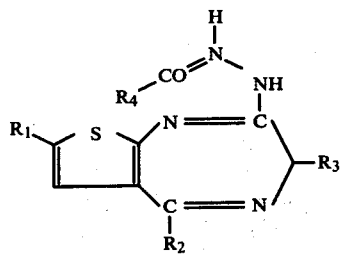

wherein $R_1$–$R_4$ are as described above or the 5-oxide thereof.

Cyclization of the compound of formula III above to yield the desired compounds of formula I or II above can be effected following conventional techniques. Thus, for example the cyclization can be brought about by heating the compound of formula III. The temperature at which the cyclization is carried out is not critical, but depends mainly upon the nature of the starting material and the reaction conditions employed. Cyclization can be effected at a temperature range of from about room temperature to about 300° C. Further, cyclization can be carried out in the presence of an inert organic solvent or in the absence of a solvent system. If the cyclization is carried out in the presence of an inert organic solvent, the preferred temperature is in the range of from about 60° C. to about 180° C. with the reflux temperature of the reaction mixture being most preferred. Alternatively, if the cyclization is carried out in the absence of a solvent system, the preferred temperature range is from about 200° to about 260° C. Suitable inert organic solvents for the present purposes include hydrocarbons, such as toluene, xylene and the like, halogenated hydrocarbons such as chlorobenzene and the like, ethers such as tetrahydrofuran, dioxane, diethyleneglycol, dimethylether, diethyleneglycol diethyl ether and the like, amides such as hexamethylphosphoric acid triamide, dimethylformamide and the like, dimethylsulfoxide and alkanols, such as methanol, ethanol, 1-propanol,2-proponal,1-butanol,2-butanol, cyclohexanol and the like; alkanols, especially methanol and ethanol, are the preferred inert organic solvents. The cyclisation time depends, of course, on the temperature used and the fact whether a solvent is present and lies between a few minutes and 48 hours. In the absence of a solvent the reaction is preferably effected in a few minutes. In the presence of a solvent the time lies preferably between 1 and 24 hours.

The starting materials of formula III above can be prepared by reacting a compound of the formula

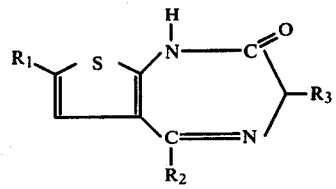

wherein $R_1$–$R_3$ are as described above or the 4-oxide thereof with a sulfide such as phosphorous pentasulfide to yield the corresponding thione of the formula

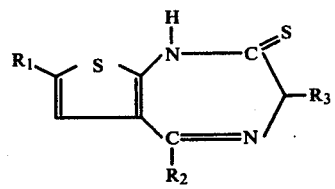

wherein $R_1$–$R_3$ are as described above or the 4-oxide thereof.

The reaction between the compound of formula IV and the sulfide such as phosphorous pentasulfide is preferably effected in the presence of an inert organic solvent. Suitable solvents for this purpose include pyridine and xylene with pyridine being the preferred solvent. This reaction is effected at a temperature in the range of from about 40° C. to the reflux temperature of the reaction mixture with the reflux temperature being preferred. In this reaction it is advantagous to use an excess of the sulfide reagent.

The thione of formula V prepared as described above is then reacted with an organic acid hydrazide of the general formula

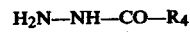

$$H_2N-NH-CO-R_4 \qquad VI$$

wherein $R_4$ is as described above to yield the desired compound of formula III.

The reaction of the thione of formula V with the acid hydrazide of formula VI is preferably carried out in the presence of an inert organic solvent. Suitable solvents for this purpose include alkanols, such as methanol, ethanol, 1 or 2-propanol, 1 or 2-butanol and the like. This reaction can be carried out at a temperature between about 60° and 120° C., most preferably at the reflux temperature of the reaction mixture. In a preferred aspect the acid hydrazide of formula VI is employed in a 2–5 fold excess over the theoretically required amount. The reaction time depends on the reaction temperature employed and lies between a few minutes and 48 hours, preferably between about 1 and 24 hours.

The crude product obtained as a result of the reaction between the compounds of formulae V and VI above consists essentially of a mixture of the compound of formula III and of the already cyclized compound of either formula I or formula II. This mixture can be separated on the basis of the different solubility properties of these compounds in organic solvents such as methylene chloride, chloroform, carbon tetrachloride, ethylacetate and the like. After separation, the compound of formula III can be cyclized as described above to yield the desired diazepine. Alternately and preferably the compound of formula III need not be isolated, but can be cyclized by heating in the manner described above to yield the desired thienotriazolodiazepine end products of formulae I and II.

In the reaction between the compounds of formulae V and VI above, it is preferable to bubble through the reaction mixture and inert gas such as nitrogen so that the hydrogen sulfide made is continuously removed. The acid hydrazides of formula VI above used in this reaction are known compounds or can be prepared in analogy to the preparation of the known material. For example, the formula VI compounds can be prepared by heating an ester of the formula $R_4$-COO-lower alkyl to reflux in the presence of hydrazine hydride using for example methanol as the solvent. The thienodiazepine derivatives of formula IV used as the starting materials for the preparation of the compounds of formula III are known compounds or can be prepared in analogy to the preparation of the known material. Thus the formula IV compound can be prepared, for example from 2-amino-3-benzoylthiophene by reaction with an α-halocarboxylic acid halide such as chloroacetyl chloride, treatment of the resulting compound with ammonia and subsequent cyclization. Where thienodiazepine derivatives of formula IV are desired in which $R_1$ and/or $R_3$ represent other than hydrogen atom and $R_2$ represents other than a phenyl group, then depending on the desired substituent the reaction can be carried out using appropriately substituted amino aroylthiophene derivatives and/or substituents can be introduced at one of subsequent stages according to methods known in the art.

Alternatively, the starting materials of formula III above can be prepared by reacting a compound of the formula

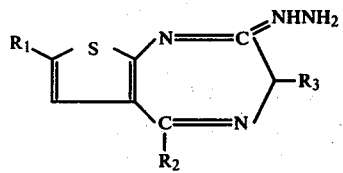

wherein $R_1$-$R_3$ are as described above or a 4-oxide thereof with a carboxylic acid or a reactive derivative thereof of the formula $R_4$—COOH     VIII wherein $R_4$ is as described above.

Suitable reactive derivatives of the foregoing carboxylic acids of formula VIII include, for example the esters, anhydrides, halides, amides, iminoethers, amidines and orthoesters with the orthoesters being especially preferred. Examples of such orthoesters are orthoacetic acid trimethylester, orthoacetic acid triethylester, orthoformic acid triethylester, orthopropionic acid triethylester, orthobutyric acid triethylester and the like.

The reaction between the compound of formula VII and the carboxylic acid or reactive derivative thereof of formula VIII is preferably effected in the presence of an inert organic solvent and an acid catalyst such as a hydrohalic acid, for example hydrochloric acid or para-toluenesulfonic acid. Suitable solvents for this purpose include alkanols such as methanol, ethanol and the like, ethers such as tetrahydrofuran, diethyl ether and the like, dimethylsulfoxide, dimethylformamide and the like. Temperature is not critical to this reaction, so that temperatures between 30° C. and the reflux temperature of the reaction mixture can be employed with the reflux temperature being preferred.

In a further alternative, the starting materials of formula III above can be prepared by reacting a compound of the general formula

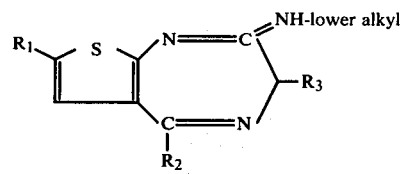

wherein $R_1$-$R_3$ are as described above or the 4-oxide thereof with an acid hydrazide of formula VI above. This reaction between the compounds of formula VI and IX is preferably effected in the presence of an inert organic solvent. Suitable solvents include alkanols such as ethanol, propanol, butanol and the like, dimethylformamide, ethers such as diglyme and methoxyethanol. Preferably this reaction is carried out in the presence of a strong base such as an amine, for example a tertiary amine, such as triethylamine, methylpiperidine and the like. This reaction is conducted at an elevated temperature, preferably at the reflux temperature of the reaction mixture.

The compounds of formula IX above can be readily prepared from the corresponding thienodiazepine derivative of formula IV by treatment with a lower alkylamine in the presence of a Lewis acid such as titanium tetrachloride.

The compounds of formula VII above can be prepared from the corresponding compound of formula IX by reaction, following standard techniques, with nitrous acid to give the corresponding N-nitroso compound. The so-obtained N-nitroso compound is then reacted with hydrazine to yield the compound of formula VII.

The compounds of formula VII above can alternatively be prepared by reacting a compound of formula V above with hydrazine.

B. In a further process aspect of the present invention the compound of formula I above can be prepared by cyclizing a compound of the general formula

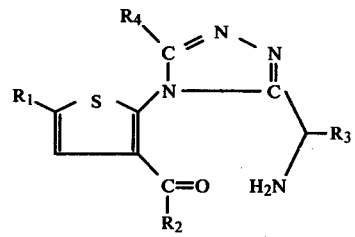

wherein $R_1$-$R_4$ are as described above.

The cyclization of the compound of formula X to yield the desired compound of formula I is carried out following conventional techniques, thus for example the cyclization can be carried out by heating a compound of formula X in the presence of an organic medium, preferably in the presence of an organic acid. The cyclization can be carried out, for example by heating the compound of formula X at the reflux temperature of the reaction mixture for several hours in a solution of an aliphatic carboxylic acid such as formic acid or acetic acid in the presence of an alkanol such as ethanol, or n-propanol, or alternatively by heating the compounds of formula X for a relatively short time, for example from about 5 minutes to about 30 minutes in the presence of an aliphatic carboxylic acid such as acetic acid, isobutyric acid or pivalic acid.

The starting materials of formula X above can be prepared in accordance with the following reaction scheme, which illustrates the preparation of such compounds in which $R_1$ and $R_3$ signify hydrogen, $R_2$ signifies phenyl and $R_4$ is as described above.

acid, propionic acid, benzene sulfonic acid, para-toluene sulfonic acid and the like. The so-obtained crude product is subsequently reacted with an alphahaloacetic halide such as chloroacetyl chloride, bromoacetyl bromide and the like in an inert organic solvent with ice-cooling or at a temperature below the boiling point of the solvent to give the compound of formula XIII. Suitable solvents for this purpose include chloroform, methylene chloride, ether, dimethylformamide, pyridine, acetic acid, mono-chloroacetic acid or mixtures of such solvents with water. If a neutral solvent is used the reaction is preferably carried out in the presence of an

REACTION SCHEME I

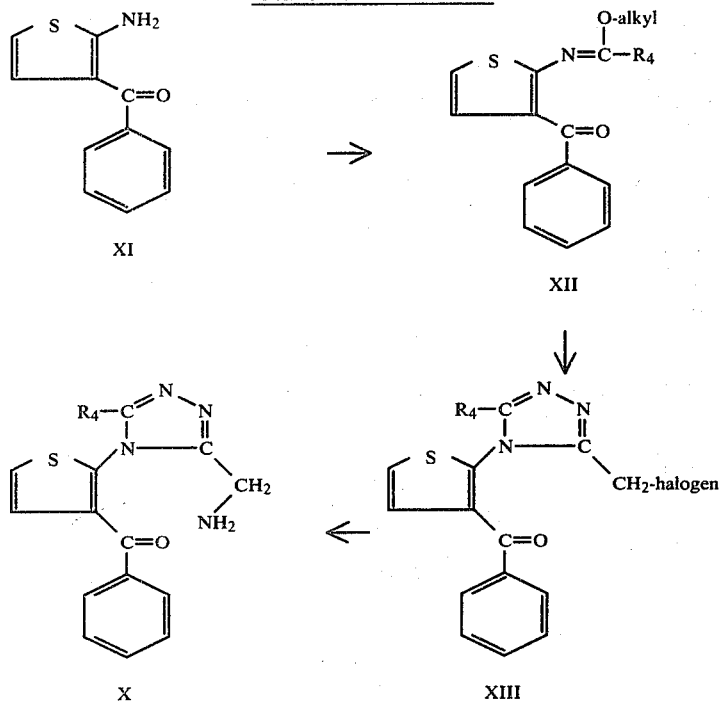

The 2-amino-3-benzoylthiophene of formula XI is converted to a compound of formula XII by treatment with an orthoester of the general formula $R_4$-C(O-alkyl)$_3$ in which $R_4$ is as described above. Treatment of the formula XI compound with an orthoester is preferably effected in the presence of an inert organic solvent, such as benzene, toluene and the like and an acid catalyst such as hydrochloric acid, sulfuric acid, acetic acid, propionic acid, benzene sulfonic acid, paratoluene sulfonic acid and the like. Temperature is not critical to this reaction so that the reaction can be carried out at a temperature between 15° and 160° C. Suitable solvents for this reaction include hydrocarbons such as benzene and toluene or alternatively the orthoester used in the reaction can be used in excess and can serve as the solvent system.

The so-obtained compound of formula XII is then reacted with hydrazine, preferably provided in a form of hydrazine hydrate in the presence of an inert organic solvent. Suitable solvents include alkanols, such as methanol, ethanol, 1-propanol, 2-propanol and the like. The reaction is carried out at a temperature between 0° C. and the reflux temperature of the reaction mixture with temperatures between about 10° and 30° C. being preferred. The reaction can be accelerated by the addition of an acid catalyst such as hydrochloric acid, hydrobromic acid, sulfuric acid, phosphoric acid, acetic acid acceptor such as sodium bicarbonate, sodium carbonate, potassium bicarbonate, potassium carbonate, pyridine, triethylamine, imidazole, 2-methylimidazole and the like.

The compound of formula XIII thus obtained is then treated with ammonia or hexamethylene tetramine to yield the desired compound of formula X. The compound of formula X so prepared need not be isolated, but can be cyclized directly to the desired compound of formula I under the reaction conditions employed for its preparation. Thus, for example the compound of formula XIII can be added to an alcoholic ammonia such as ethanolic or methanolic ammonia or a compound of formula XIII can be dissolved in an inert organic solvent and treated with liquid ammonia or hexamethylene tetramine to yield the compound of formula X. Suitable solvents for this purpose include methylene chloride, carbon tetrachloride, ethers such as tetrahydrofuran or dioxane, dimethylsulfoxide, dimethylformamide, alkanols such as methanol, ethanol, 1-propanol, 2-propanol, 1-butanol, 2-butanol and the like. The resulting compound of formula X either in crude or purified form can be cyclized as described above to yield the compound of formula I.

Where compounds of formula X are desired in which $R_1$ and/or $R_3$ represent other than a hydrogen atom and $R_2$ represents other than a phenyl group, depending on the desired substituent, the reaction can be carried out using appropriately substituted compounds of formula XI and/or substituents can be introduced according to known procedures at one of the subsequent stages and/or substituents can be converted into other substituents.

The compounds of the formulae III, V, VII, IX, X, XII and XIII are novel and as such form a part of the present invention.

C. In a further process aspect, the compounds of formulae I or II above wherein the $R_1$ substituent signifies halogen or nitro can be prepared by either halogenating or nitrating the corresponding compound of formulae I and II wherein $R_1$ signifies hydrogen.

Halogenation of the 1-unsubstituted thienotriazolodiazepines of formula I and II above is effected following the conventional technique. Thus, for example this halogenation can be carried out using elemental chlorine, bromine or iodine, sulphurylchloride and the like with the reaction conditions being primarily governed by the nature of the halogenating agent employed. Chlorination can be carried out using elemental chlorine, for example in chloroform/pyridine or nitrobenzene expediently at room temperature. Bromination can be carried out using elemental bromine, for example in chloroform at an elevated temperature, for example the reflux temperature of the reaction medium. Iodination using elemental iodine can for example be carried out in chloroform and in the presence of mercuric oxide at room temperature. Chlorination using sulphuryl chloride can, for example be carried out in chloroform or glacial acetic acid at room temperature or at an elevated temperature, for example the reflux temperature of the reaction medium.

The nitration of the 1-unsubstituted compounds of formulae I and II above is also effected following conventional techniques, for example the nitration can be effected using nitric acid or an alkali nitrate in the presence of sulfuric acid. Thus, for example the nitration can be carried out by dissolving the starting materials in concentrated sulfuric acid and treating the thus obtained solution slowly with a mixture of concentrated nitric acid and concentrated sulfuric acid. As a rule the nitration is advantageously carried out at a low temperature, for example at a temperature in the range of from about $-10°$ C. to about $+10°$ C.

D. In a further process aspect the compounds of formulae I and II above wherein $R_4$ signifies a lower alkanoyl group may be prepared by oxidizing the corresponding compound of formulae I and II, wherein $R_4$ signifies an alphahydroxy lower alkyl group.

Oxidation of the alphahydroxy lower alkyl group to yield the desired lower alkanoyl group is effected following the conventional techniques. Preferred oxidizing agents for this purpose include carbodiimides, such as dicyclohexylcarbodiimide and the like in dimethylsulfoxide or the pyridine/sulfur trioxide adduct in dimethylsulfoxide. These oxidations are carried out in the presence of an organic base such as pyridine or triethylamine. Silver oxide can also be used as the oxidizing agent, in which case it is preferably used in a water miscible inert solvent such as an alkanol or acetone. Alternatively, the oxidation can be carried out in absolute toluene using chromium trioxide in graphite or manganese dioxide. All of the foregoing oxidations, with the exception of those using chromium trioxide or manganese dioxide are preferably carried out at room temperature or at a temperature slightly above or below room temperature. When the oxidation is carried out using chromium trioxide or manganese dioxide, the oxidation mixture is advantageously heated to the reflux temperature.

E. In a further process aspect, the compounds of formulae I and II above wherein $R_4$ signifies a lower alkylcarbonyloxy lower alkyl group or an amino carbonyloxy lower alkyl group can be prepared by esterifying the corresponding compound of formulae I or II in which $R_4$ signifies a hydroxy lower alkyl group. This esterification is effected using an appropriate alkanoylating agent or with an isocyanate.

The esterification with an alkanoylating agent can be carried out, for example by reacting the hydroxy lower alkyl substituted compound with an acid halide or acid anhydride in an inert organic solvent in the presence of an organic base such as pyridine or triethylamine. Suitable solvents for this purpose include hydrocarbons such as benzene or toluene, halogenated hydrocarbons such as carbon tetrachloride, chloroform or methylene chloride or an excess of the organic base. The reaction is carried out at a temperature between about $0°$ C. and $80°$ C., preferably at between room temperature and about $60°$ C. The esterification with an isocyanate is preferably carried out in an inert organic solvent at room temperature or at a temperature slightly above or below room temperature. Suitable solvents for this purpose include benzene, methylene chloride, ethers, dioxane and the like.

F. This process aspect is directed to the preparation of the compounds of formulae I or II above in which $R_4$ signifies lower alkoxy lower alkyl, aralkoxy lower alkyl or lower alkyl thio lower alkyl or a group of the formulae -lower alkyl-Z in which Z is as described above. The compounds of formulae I and II above so substituted in the 9-position can be prepared by reacting the corresponding compound which carries a group of the formula -lower alkyl-A in the 9-position with a compound of the formula BR; in which formulae I of the symbols A or B represents a hydroxy or mercapto group or the grouping -NH-$R_7$ wherein $R_7$ is as described above and the other symbol A or B represents a leaving atom or a leaving group and R signifies a lower alkyl group provided that when the symbol B represents the group -NH-$R_7$, R can also represent a hydrogen atom or a hydroxy lower alkyl group or R and $R_7$ taken together with their attached nitrogen atom can represent a saturated 5-6-membered heterocyclic ring, which may contain a further nitrogen atom or an oxygen atom and provided that when one of the symbols A and B represents a hydroxy group, R can also represent an aralkyl group.

Suitable leaving atoms or leaving groups for the present purpose include a halogen atom, preferably a chlorine atom or a reactive ester group, for example a methane sulfonic acid ester group. When one of the symbols A or B represents a hydroxy or mercapto group, these compounds can be prepared following known procedures for the preparation of an ether or thioether function. The manufacture of the thioether, i.e., the compound of formulae I and II in which $R_4$ represents a lower alkylthio lower alkyl group can be carried out, for example by converting a corresponding compound of formulae I or II in which $R_4$ represents a hydroxy lower alkyl group into the methane sulfonic acid ester and reacting this ester with a thio alcohol or a corresponding mercaptide. This reaction is carried out in the presence of a suitable solvent such as dimethylformamide, dioxane or tetrahydrofuran at a temperature between room temperature and 100° C. preferably at about 50° C.

Where B represents the grouping -NH-$R_7$ and R represents a lower alkyl group or has any of the additional meanings mentioned above, these compounds can be prepared using standard techniques for the preparation of amino lower alkyl substituted compounds. For example, a compound of formulae I or II above in which $R_4$ represents a hydroxy lower alkyl group can be converted into the methane sulfonic acid ester and this ester can be reacted with an amine of the general formula $HNR_7R_8$ in which $R_7$ and $R_8$ are as described above. The reaction is carried out following conventional techniques, preferably in the presence of a suitable inert organic solvent such as dimethylformamide or an alcohol such as methanol or ethanol at a temperature between 0° C. and 100° C., preferably at between 0° and 5° C.

G. In a further process aspect, compounds of formulae I and II above wherein $R_4$ signifies a lower alkylcarbonyloxy lower alkyl group or a dilower alkylaminocarbonyloxy lower alkyl group can be prepared by reacting the corresponding compound of formulae I or II wherein $R_4$ signifies a hydroxy lower alkyl group with a reactive derivative of an acid of the general formula HO-CO-lower alkyl or HO-CO-N-(lower alkyl)$_2$.

Examples of reactive derivatives of the aforementioned acids are halogenides especially chlorides as well as anhydrides of the acids of the general formula HO-CO-lower alkyl. The acetylation of the hydroxy lower alkyl group noted as the $R_4$ substituent is effected following conventional techniques, for example the acetylation can be carried out by dissolving the compounds in a suitable inert organic solvent, for example pyridine, treating the solution with an appropriate anhydride and then leaving the mixture to stand for some time at room temperature or at a slightly higher temperature.

The formation of a dilower alkyl amino carbonyloxy lower alkyl group is also carried out following conventional techniques. Thus, for example the hydroxy lower alkyl substituted compound can be converted into an alcoholate in the presence of a suitable solvent such as dioxane, then treating this alcoholate with an N,N-dilower alkyl carbamoyl chloride and then warming the mixture for a short period of time.

H. In a further process aspect the compounds of formulae I and II above wherein $R_4$ signifies a lower alkoxy carbonyl amino lower alkyl group can be prepared by reacting the corresponding compound which carries the group of the formula -lower alkyl-K in place of the $R_4$ substituent with the compound of the general formula L-CO-O-lower alkyl in which formulae I of the symbols K and L represents an amino group and the other symbol represents a leaving atom or group. The lower alkoxy carbonyl amino lower alkyl group can be formed following the conventional techniques. Thus, for example this group can be formed by reacting an amino lower alkyl substituted compound with a chloroformic acid lower alkyl ester in the presence of a suitable inert solvent such as dioxane. The reaction is advantageously carried out at room temperature.

I. In a further process aspect of the present invention, the compounds of formulae I and II above wherein $R_4$ signifies a primary hydroxy lower alkyl group can be prepared by reducing the corresponding compound in which $R_4$ signifies a lower alkoxy carbonyl or lower alkoxy carbonyl lower alkyl group. This reduction can be carried out following the conventional techniques, for example by treating the appropriate starting material with a complex hydride, such as lithium aluminum hydride.

The compounds of formulae I and II above form acid addition salts with pharmaceutically acceptable organic and inorganic acids. Suitable acids for the purposes of the present invention include hydrochloric acid, hydrobromic acid, nitric acid, sulfuric acid, phosphoric acid, tartaric acid, citric acid, maleic acid, ascorbic acid, formic acid, acetic acid, succinic acid, methane sulfonic acid, benzene sulfonic acid, para-toluene sulfonic acid and the like.

Compounds of formulae I and II above as well as the pharmaceutically acceptable acid addition salts are useful as anticonvulsants, sedatives and muscle relaxants, tranquilizers and anxiolytics. Their useful anticonvulsant activity is demonstrated in warm blooded animals utilizing the standard antipen-tetrazole test. In this test following the method of Orloff (*Proc. Soc. Exptl. Biol. Med.*, 70, 254–257, 1949), 2-chloro-4-(orthochlorophenyl)9-methyl-6H-thieno[3,2-f]-f-triazolo[4,3-a][1,4]diazepine exhibits an $APR_{2.0}$ of 0.03–0.1 mg/kg p.o.. By $APR_{2.0}$ is understood that dose in mg/kg of an anti-convulsant which brings about double the pentetrazole consumption in comparison to the untreated control group.

The muscle relaxant activity of the compounds of formulae I and II above is demonstrated in warm blooded animals utilizing the standard rotating rod test. For example, the above mentioned 2-chloro-4-(orthochlorophenyl)-9-methyl-6H-thieno[3,2-f]-s-triazolo[4,3-a][1,4]diazepine shows an $HD_{50}$ of 0.5 mg/kg p.o. (mouse).

The compounds of formulae I and II and their pharmaceutically acceptable acid addition salts can be made up into pharmaceutical preparations (e.g. tablets, dragees, suppositories, capsules, solutions, suspensions, emulsions etc) according to generally known procedures. Apart from the usual pharmaceutically inert carrier materials such as, for example, lactose, starch, talc, magnesium stearate, water, vegetable oils, polyalkyleneglycols and the like, these preparations can also contain preservatives, stabilizers, wetting agents, emulsifiers, salts for varying the osmotic pressure, buffers or other therapeutically valuable materials. If necessary, the pharmaceutical preparations can be sterilized or can be subjected to other operations usual in the pharmaceutical industry. The dosage follows individual requirements but a dosage of from about 0.1 mg/kg to about 30 mg/kg is preferred. If the drug is administered in parenteral form, a dosage in the range of 0.1 mg/kg to about 10 mg/kg is preferred. Suitable pharmaceutical dosage forms can contain from 1 to 50 mg of the active ingredient of formulae I or II.

The following examples are presented to further illustrate the present invention. Unless otherwise indicated all temperatures are given in degrees Centigrade.

EXAMPLE 1

2.5 g of 2-(2-acetylhydrazino)-7-chloro-5-(o-chlorophenyl)-3H-thieno[2,3-e]-1,4-diazepine are heated under reduced pressure (water-jet vacuum) for 5–7 minutes in an oil bath (250° C.) until gas evolution is no longer observed. The resulting product is finely triturated in a mortar and boiled out several times with a total of 400 ml of ethyl acetate. After removal of the solvent, the resulting crude product is recrystallised from ethanol containing active carbon to give 2-chloro-4-(o-chlorophenyl)-9-methyl-6H-thieno[3,2-f]-s-triazolo[4,3-a][1,4]diazepine in the form of cream-colored crystals, melting point 205°–206° C.

The starting material can be prepared as follows:

3.1 g (0.01 mol) of 7-chloro-5-(o-chlorophenyl)-1,3-dihydro-2H-thieno[2,3-e]-1,4-diazepin-2-one are heated to reflux for 30 minutes with 2.45 g of phosphorus pentasulphide in 100 ml of absolute pyridine, dry nitrogen being conducted through the solution. The solution is separated on a 35 cm long column ($\phi$3.5 cm) filled with 100 g of Silica gel [(0.05 to 0.2 mm) (Merck)]. The separation is followed by thin-layer chromatography (eluant: benzene/ethanol 9:2). When impurity, which runs substantially slower, appears the elution is stopped. The solvent is removed under a vacuum, whereby 7-chloro-5-(o-chlorophenyl)-1,3-dihydro-2H-thieno[2,3-e]-1,4-diazepine-2-thione immediately crystallizes out in the form of yellow crystals of melting point 223°–225° C.

3.3 g (0.01 mol) of 7-chloro-5-(o-chlorophenyl)-1,3-dihydro-2H-thieno[2,3-e]-1,4-diazepine-2-thione are heated to reflux for 30 minutes under a nitrogen atmosphere with 2.5 g of acetic acid hydrazide and 150 ml of n-butanol. The solvent is removed under a vacuum, the residue treated with 200 ml of ethyl acetate and shaken out three times with 200 ml of water each time. The precipitated starting material is filtered under a vacuum and combined with the ethyl acetate phase. After concentration of the solution to 50 ml, the product is left to crystallize.

The product is recrystallized from ethyl acetate containing active carbon to give 2-(2-acetylhydrazino)-7-chloro-5-(o-chlorophenyl)-3H-thieno[2,3-e]-1,4-diazepine in the form of orange crystals, melting point 211°–213° C.

EXAMPLE 2

7.5 g (0.029 mol) of 1,3-dihydro-5-phenyl-2H-thieno[2,3-e]-1,4-diazepine-2-thione are heated to reflux for 4 hours under a nitrogen atmosphere with 6.4 g (0.087 mol) of acetyl hydrazine in 500 ml of n-butanol. The solution initially becomes dark red-brown (30 minutes), but subsequently becomes distinctly lighter. The solvent is evaporated under a vacuum, the residue taken up in 150 ml of methylene chloride and extracted portionwise with a total of 1 liter of 1-N hydrochloric acid. Then, sufficient ether is added such that the organic phase comes to the surface and the mixture is again extracted with a total of 1 liter of 1-N hydrochloric acid.

The aqueous phase is neutralized with sodium bicarbonate and shaken out three times with methylene chloride. The organic phase is subsequently dried over sodium sulphate. After evaporation of the solvent, the residue is treated with ethyl acetate, crystallized, filtered under a vacuum and recrystallized from ethyl acetate containing active carbon to give 9-methyl-4-phenyl-6H-thieno[3,2-f]-s-triazolo[4,3-a][1,4]diazepine as colorless crystals, melting point 224°–226° C.

The starting material can be prepared as follows:

12.1 g (0.05 mol) of 1,3-dihydro-5-phenyl-2H-thieno[2,3-e]-1,4-diazepin-2-one are heated to reflux for 35 minutes with 12.2 g (0.055 mol) of phosphorus pentasulphide in 400 ml of absolute pyridine, dry nitrogen being conducted through the solution. The solution is concentrated to 200 ml and the mixture separated on a 70 cm long column ($\phi$3.5 cm) filled with 250 g of Silica gel [0.05 to 0.2 mm (Merck)]. The solution is concentrated under a vacuum and yields 1,3-dihydro-5-phenyl-2H-thieno[2,3-e]-1,4-diazepine-2-thione in the form of yellow crystals, melting point 208°–210° C.

EXAMPLE 3

1.5 g (0.00582 mol) of 1,3-dihydro-5-phenyl-2H-thieno[2,3-e]-1,4-diazepine-2-thione are heated to reflux for 4 hours under a nitrogen atmosphere with 1.3 g (0.0175 mol) of acetyl hydrazine in 120 ml of absolute ethanol. The solvent is evaporated and the crystals obtained are shaken with water in a separating funnel. After filtration under a vacuum, the product is recrystallized from ethyl acetate containing active carbon to give colorless crystals of 2-(2-acetylhydrazino)-5-phenyl-3H-thieno[2,3-e]-1,4-diazepine, melting point 194°–196° C. (transition).

EXAMPLE 4

0.2 g of 7-chloro-1,3-dihydro-5-(o-nitrophenyl)-2H-thieno[2,3-e]-1,4-diazepine-2-thione are heated to reflux for 5 hours under a nitrogen atmosphere with 0.2 g of acetic acid hydrazide in 30 ml of n-butanol. After evaporation of the solvent, the product is taken up in methylene chloride and extracted several times with 1-N hydrochloric acid, the organic phase being treated portionwise with ether such that it comes to the surface in the separating funnel. After neutralization of the aqueous phase with sodium bicarbonate, the mixture is extracted with methylene chloride, the solvent evaporated after drying over sodium sulphate and the residue made into a paste with ethyl acetate. The resulting crystals are recrystallized from ethyl acetate containing active carbon to give colorless crystals of 2-chloro-9-methyl-4-(o-nitrophenyl)-6H-thieno[3,2-f]-s-triazolo[4,3-a][1,4]diazepine, melting point 210°–212° C.

The starting material can be prepared as follows:

1 g (0.00327 mol) of 7-chloro-1,3-dihydro-5-(o-nitrophenyl)-2H-thieno[2,3-e]-1,4-diazepin-2-one are heated to reflux with 0.8 g of phosphorus pentasulphide in 30 ml of absolute pyridine, nitrogen being conducted through the solution. The mixture is separated on a column ($\phi$3 cm) filled with 50 g of Silica gel[(0.05 to 0.2 mm) (Merck)] (the product travelling on the front and the impurities travelling only slowly). After concentration of the pyridine solution under a vacuum, the residue is treated with methylene chloride and brought to crystallization. After completion of the crystallization in a refrigerator, the mixture is filtered under a vacuum and washed with a small amount of ice-cold methylene chloride. Recrystallization from absolute methanol yields 7-chloro-1,3-dihydro-5-(o-nitrophenyl)-2H-thieno[2,3-e]-1,4-diazepine-2-thione in the form of yellow crystals, melting point 213°–215° C.

EXAMPLE 5

225 g (0.72 mol) of 2-chloroacetylamino-3-(o-chlorobenzoyl)-thiophene are dissolved in 2 liters of acetone and 118 g of sodium iodide are added. The solution is heated to reflux for 1.5 hours, with sodium chloride precipitating out. The mixture is evaporated, treated with 3 liters of methylene chloride and covered in a 10 liter reaction vessel with 3 liters of concentrated aqueous ammonia. The mixture is then stirred for 48 hours in such a manner that the layers do not intermix. At the end of the reaction, the phases are separated, the aqueous phase extracted twice with 200 ml of methylene chloride each time and the organic phase washed three times with water. The methylene chloride phase is evaporated and brought to crystallization. The crystal cake is treated with 200 ml of methylene chloride and boiled out with stirring. The product is left overnight in a refrigerator to crystallize, filtered under a vacuum and washed with ice-cold methylene chloride to give 2-aminoacetylamino-3-(o-chlorobenzoyl)-thiophene, melting point 156°–158° C.

150 g (0.51 mol) of 2-aminoacetylamino-3-(o-chlorobenzoyl)-thiophene are dissolved in 2.5 liters of absolute ethanol and 250 ml of glacial acetic acid are added. The solution is heated to reflux with stirring until the reaction has ended (about 5 hours) as indicated by thin-layer chromatography (eluant: ether). The solvent is removed under a vacuum and the product taken up in 2 liters of methylene chloride. The methylene chloride solution is shaken out with dilute aqueous sodium bicarbonate solution, washed with water and evaporated. The product is brought to crystallization, treated with 150 ml of methylene chloride, refluxed and left to crystallize in a refrigerator. After filtration under a vacuum and treatment with ice-cold methylene chloride, pure 5-(o-chlorophenyl)-1,3-dihydro-2H-thieno[2,3-e]-1,4-diazepin-2-one is obtained in the form of bright-yellow crystals, melting point 221°–223° C.

EXAMPLE 6

3.0 g of 7-chloro-1,3-dihydro-5-(o-trifluoromethylphenyl)-2H-thieno[2,3-e]-1,4-diazepin-2-one are dissolved in 50 ml of diethyleneglycol dimethyl ether at 80° C., treated with 4.2 g of phosphorus pentasulphide and 3 g of finely triturated sodium bicarbonate and warmed for 15 minutes at 80°–85° C. The mixture is then evaporated under a vacuum and taken up in 60 ml of butanol. 3 g of acetyl hydrazine are added and the mixture is heated under reflux for 90 minutes. The butanol is evaporated under a vacuum, the residue taken up in methylene chloride, the organic phase shaken out several times with water, dried and evaporated. The oily residue is crystallized from ether to yield 2-chloro-9-methyl-4-(o-trifluoromethylphenyl)-6H-thieno[3,2-f]-s-triazolo[4,3-a]-[1,4]diazepine which, after recrystallization from ethyl acetate, has a melting point of 193°–195° C.

EXAMPLE 7

6.8 g of 2-(2-acetylhydrazino)-7-chloro-5-(o-fluorophenyl)-3H-thieno[2,3-e]-1,4-diazepine are refluxed for 9 hours in 300 ml of absolute xylene. After cooling, the precipitated impurities are filtered off under vacuum. The solvent is then evaporated under reduced pressure and the product recrystallized from ethyl acetate containing active carbon to yield 2-chloro-4-(o-fluorophenyl)-9-methyl-6H-thieno[3,2-f]-s-triazolo[4,3-a][1,4]diazepine, melting point 187°–189° C.

The starting material is prepared as follows:

10 g of 7-chloro-5-(o-fluorophenyl)-1,3-dihydro-2H-thieno[2,3-e]-1,4-diazepin-2-one are dissolved in 150 ml of diethyleneglycol dimethyl ether at 55° C. and stirred with a mixture of 15 g of finely triturated phosphorus pentasulphide and 10 g of sodium bicarbonate for 40 minutes. The solvent is distilled off and the residue washed with water, filtered under vacuum and dried. The 7-chloro-5-(o-fluorophenyl)-1,3-dihydro-2H-thieno[2,3-e]-1,4-diazepine-2-thione thus obtained is refluxed in 200 ml of methanol with 15 g of acetyl hydrazine for 30 minutes. On cooling, 2-(2-acetylhydrazino)-7-chloro-5-(o-fluorophenyl)-3H-thieno[2,3-e]-1,4-diazepine precipitates. The methanol is distilled off and the residue partitioned between methylene chloride and water. The solvent is evaporated under reduced pressure and the residue crystallized from methanol to yield a second crop of 2-(2-acetylhydrazino)-7-chloro-5-(o-fluorophenyl)-3H-thieno[2,3-e]-1,4-diazepine, melting point 207°–209° C.

EXAMPLE 8

9.1 g (0.03 mol) of 1,3-dihydro-5-(o-nitrophenyl)-2H-thieno[2,3-e]-1,4-diazepine-2-thione are refluxed with 500 ml of absolute butanol and 9 g of acetic hydrazide, a stream of nitrogen being conducted through the solution. After 2 hours, the solvent is evaporated and the residue taken up in 300 ml of methylene chloride and washed three times with 100 ml of water each time. After drying and evaporation of the organic phase and trituration with ethyl acetate, there is obtained crystalline 9-methyl-4-(o-nitrophenyl)-6H-thieno[3,2-f]-s-triazolo[4,3-a][1,4]diazepine which, after recrystallization from ethanol and treatment with active carbon, melts at 260°–262° C.

The starting material is prepared as follows:

15.7 g (0.055 mol) of 1,3-dihydro-5-(o-nitrophenyl)-2H-thieno[2,3-e]-1,4-diazepin-2-one are warmed to 60° C. in 40 ml of absolute pyridine and there are added with vigorous stirring 15.7 g of finely powdered phosphorus pentasulphide. The mixture is stirred for a further 1.5 hours at this temperature, subsequently poured on to 500 g of ice and 500 ml of water with vigorous stirring and stirred for 2 hours. The resulting precipitate is filtered under a vacuum and washed with a large amount of water. The precipitate is suspended in water and shaken out thoroughly with 500 ml of methylene chloride each time. After drying, the organic phase is evaporated under reduced pressure and the residue refluxed with a small amount of chloroform. After completion of the crystallization in a refrigerator, there is obtained 1,3-dihydro-5-(o-nitrophenyl)-2H-thieno[2,3-e]-1,4-diazepine-2-thione which, after recrystallization from absolute methanol, melts at 207°–209° C.

EXAMPLE 9

2.2 g of 2-(2-acetylhydrazino)-7-chloro-5-(2-pyridyl)-3H-thieno[2,3-e]-1,4-diazepine are refluxed for 2 hours in 120 ml of absolute xylene. The solution is then cooled and the precipitated impurities are filtered off. The solvent is evaporated under reduced pressure and there is obtained 2-chloro-9-methyl-4-(2-pyridyl)-6H-thieno[3,2-f]-s-triazolo[4,3-a][1,4]diazepine in the form of a crystalline product which, after recrystallization from ethyl acetate, melts at 174°–176° C.

The starting material is prepared as follows:

14.6 g of cyanomethyl-2-pyridyl-ketone and 7.6 g of bismercaptoacetaldehyde are dissolved or suspended in 60 ml of absolute dioxane and treated with 5 ml of triethylamine with stirring. After a period of 1.5 hours at room temperature, the mixture is poured into about 500 ml of water and extracted with methylene chloride. The methylene chloride phase is shaken out twice with 1-N sodium hydroxide, dried over sodium sulphate with the addition of active carbon and evaporated. There is obtained 2-amino-3-thienyl-2'-pyridyl-ketone, which, after recrystallization from benzene, yields yellow crystals of melting point 122°–124° C.

65 g of 2-amino-3-thienyl-2'-pyridyl-ketone are dissolved in 500 ml of dry dioxane and 80 g of potassium carbonate are suspended in the solution which is then treated with 80 g of chloroacetyl chloride. After the exothermic reaction has slowed down, the mixture is stirred for a further 2 hours at room temperature and then poured into a solution of 50 g of potassium carbonate in 2 liters of water. The precipitate which separates is filtered under a vacuum, washed with water and taken up in methylene chloride. After drying over sodium sulphate containing active carbon, the solvent is distilled off under a vacuum, the residue washed with a small amount of methanol and filtered under a vacuum to yield 2-chloroacetylamino-3-thienyl-2'-pyridyl-ketone which, after crystallization from methanol, is in the form of yellow needles, melting point 130°–132° C.

76 g of 2-chloroacetylamino-3-thienyl-2'-pyridyl-ketone are dissolved in 1 liter of acetone and, after the addition of 45 g of sodium iodide, stirred for 15 hours at room temperature. The acetone solution is then evaporated to dryness under vacuum and the residue partitioned between about 300 ml of methylene chloride and water, the organic phase covered with about 1.5 liters of concentrated ammonia and stirred for 48 hours without mixture of the phases. After completion of the reaction, the phases are separated, the organic phase evaporated to dryness and the residue taken up in methylene chloride. This solution is thoroughly extracted with 0.1-N hydrochloric acid, the aqueous extracts neutralized with potassium carbonate and the separated solid material filtered under a vacuum and dried. After crystallization from ethanol, there is obtained 2-aminoacetylamino-3-thienyl-2'-pyridyl-ketone in the form of yellow crystals of melting point 259°–262° C.

A solution of 32.4 g of 2-aminoacetylamino-3-thienyl-2'-pyridyl-ketone in 350 ml of acetic acid is heated under reflux for 15 minutes. The solvent is then distilled off under vacuum, the residue washed with a small amount of methylene chloride and the solid material filtered under vacuum. After crystallization from ethanol, there is obtained 1,3-dihydro-5-(2'-pyridyl)-2H-thieno[2,3-e]-1,4-diazepin-2-one in the form of colorless crystals, melting point 263°–266° C. (decomposition).

9.8 g of 1,3-dihydro-5-(2'-pyridyl)-2H-thieno[2,3-e]-1,4-diazepin-2-one are dissolved in 350 ml of acetic acid and treated dropwise at room temperature with stirring with a solution of 8.0 g of sulphuryl chloride in 20 ml of acetic acid. After completion of the addition, the mixture is stirred for a further 15 hours. The separated yellow solid material is filtered under vacuum, dissolved in water and the solution neutralized with sodium bicarbonate. The yellow-green solid material which separates is filtered under vacuum, washed with water and dried. After crystallization from ethanol, there is obtained 7-chloro-1,3-dihydro-5-(2-pyridyl)-2H-thieno[2,3-e]-1,4-diazepin-2-one in the form of yellowish-green crystals, melting point 250°–252° C. (decomposition).

3.5 g of 7-chloro-1,3-dihydro-5-(2-pyridyl)-2H-thieno-[2,3-e]-1,4-diazepin-2-one are dissolved in 200 ml of diethyleneglycol dimethyl ether at 65° C. and stirred for 30 minutes with 5 g of finely triturated phosphorus pentasulphide. The solvent is then distilled off and the residue taken up in methylene chloride and shaken out three times with water. The organic phase is dried and evaporated. The 7-chloro-1,3-dihydro-5-(2-pyridyl)-2H-thieno[2,3-e][1,4]diazepine-2-thione is dissolved in 200 ml of methanol and boiled for 30 minutes with 6 g of acetyl hydrazine. The solvent is distilled off and the residue taken up in methylene chloride and shaken three times with water. The methylene chloride is distilled off and the crystalline residue washed with methanol. After crystallization from methanol, there is obtained 2-(2-acetylhydrazino)-7-chloro-5-(2-pyridyl)-3H-thieno[2,3-e]-1,4-diazepine, melting point 193°–195° C.

EXAMPLE 10

2 g (0.0069 mol) of 5-(o-chlorophenyl)-2-hydrazino-3H-thieno[2,3-e]-1,4-diazepine are suspended in 200 ml of dry methylene chloride and treated with 10 g of sodium bicarbonate. The solution is cooled to 0° C. and treated with stirring with 0.8 ml of acetyl chloride. After 45 minutes, the solid material is filtered off from the solution which is then shaken out twice with 100 ml of water each time. After drying over sodium sulphate, the organic phase is evaporated and treated with 100 ml of butanol, whereupon 20 ml thereof are evaporated off under reduced pressure. The solution is refluxed for 8 hours and evaporated under vacuum. After trituration of the oily residue with ethanol, the resulting crystals are refluxed with a small amount of ethanol, left to crystallize in a refrigerator, filtered under a vacuum and dried to yield 4-(o-chlorophenyl)-9-methyl-6H-thieno[3,2-f]-s-triazolo[4,3-a][1,4]diazepine, melting point 221°–223° C.

The starting material is prepared as follows:

1.5 g (0.00545 mol) of 7-chloro-1,3-dihydro-5-phenyl-2H-thieno[2,3-e]-1,4-diazepin-2-one are suspended in 40 ml of diethyleneglycol dimethyl ether, warmed to 75° C. with stirring and a mixture of 2.2 g of phosphorus pentasulphide and 1.5 g of sodium bicarbonate, which has been finely triturated, is added. The mixture is stirred for a further hour and the solvent is removed under vacuum. The remaining oil is treated with ice and water, the crystalline residue filtered under a vacuum and washed with a large amount of water. The precipitate is suspended in 150 ml of water and shaken out five times with 100 ml of methylene chloride each time. After drying over sodium sulphate, the organic phase is evaporated and the crystalline residue recrystallized from absolute methanol to yield 7-chloro-1,3-dihydro-5-phenyl-2H-thieno[2,3-e]-1,4-diazepine-2-thione which melts at 223°–225° C. (decomposition).

1.1 g (0.00376 mol) of 7-chloro-1,3-dihydro-5-phenyl-2H-thieno[2,3-e]-1,4-diazepine-2-thione are dissolved in 400 ml of absolute methanol with warming and 1 ml of 100% hydrazine hydrate is added. The solution is concentrated to 50 ml and left to crystallize in a refrigerator. After filtration under vacuum and drying, there is obtained 7-chloro-2-hydrazino-5-phenyl-3H-thieno[2,3-e]-1,4-diazepine as colorless crystals, melting at 204°–207° C. (decomposition from 185° C.).

EXAMPLE 11

0.35 g of 2-(2-acetylhydrazino)-7-chloro-5-(2,6-difluorophenyl)-3H-thieno[2,3-e]-1,4-diazepine are distributed on a metal plate in as thin as possible a layer and maintained at 270° C. for 1 minute in a sand bath. The melt is taken up in methylene chloride and shaken three times with 0.1-N hydrochloric acid in order to remove the starting material. The methylene chloride is distilled off and the product recrystallized from ethyl acetate containing active carbon. There is obtained 2-chloro-4-

(2,6-difluorophenyl)-9-methyl-6H-thieno[3,2-f]-s-triazolo[4,3-a][1,4]diazepine, melting point 185°–187° C.

The starting material is prepared as follows:

0.06 g of 7-chloro-5-(2,6-difluorophenyl)-1,3-dihydro-2H-thieno[2,3-e]-1,4-diazepin-2-one are introduced into 25 ml of diethyleneglycol dimethyl ether and warmed to 85° C. 0.85 g of finely triturated phosphorus pentasulphide are added to the solution which is then stirred for 35 minutes at 85° C. The solvent is then evaporated under reduced pressure, the residue taken up in 80 ml of methylene chloride and shaken three times with water. The organic phase is evaporated, the crude 7-chloro-5-(2,6-difluorophenyl)-1,3-dihydro-2H-thieno-[2,3-e]-1,4-diazepine-2-thione taken up in 20 ml of methanol and refluxed for 40 minutes with 1 g of acetyl hydrazine. The product which precipitates in crystalline form is filtered off under vacuum and rinsed with methanol. In order to obtain further product, the mother liquor is evaporated, the residue taken up in methylene chloride and shaken out three times with 0.1-N hydrochloric acid. The hydrochloric acid phase is neutralized with sodium bicarbonate and shaken out with methylene chloride. The organic phase is dried and evaporated under reduced pressure. The 2-(2-acetylhydrazino)-7-chloro-5-(2,6-difluorophenyl)-3H-thieno[2,3-e]-1,4-diazepine thus-obtained melts at 257°–260° C. after crystallization from methanol.

EXAMPLE 12

3.5 g (0.0111 mol) of 4-(o-chlorophenyl)-9-methyl-6H-thieno[3,2-f]-s-triazolo[4,3-a][1,4]diazepine are finely triturated and dissolved in 35 ml of sulphuric acid at 5° C. At 0° C. a nitrating acid mixture (0.805 ml of 65% nitric acid and 1.6 ml of sulphuric acid) cooled to 0° C. is added dropwise within 0.5 hour. The mixture is stirred for a further 2.5 hours at 0° C. and subsequently poured on to 500 g of ice and 500 ml of water. The solution is neutralized with solid sodium bicarbonate, whereupon the product precipitates in crystalline form. The product is then shaken out three times with 200 ml of methylene chloride each time, the organic phase washed once again with water and dried. After evaporation of the solvent; the residue is triturated with ethyl acetate and the resulting 4-(o-chlorophenyl)-9-methyl-2-nitro-6H-thieno[3,2-f]-s-triazolo[4,3-a][1,4]diazepine recrystallized from ethanol containing active carbon. The product obtained melts at 270°–272° C.

EXAMPLE 13

7-Chloro-1,3-dihydro-5-(o-nitrophenyl)-2H-thieno-[2,3-e]-1,4-diazepine-2-thione, obtained from 4 g (0.013 mol) of 7-chloro-1,3-dihydro-5-(o-nitrophenyl)-2H-thieno[2,3-e]-1,4-diazepin-2-one, is taken up in 600 ml of methylene chloride and treated with sodium sulphate until completely dry. An oily residue which may be present is dissolved in 20 ml of methanol and the solution filtered. 6.85 g (a 5-fold molar amount) of methoxyacetic acid hydrazide are then added and the solution is completely evaporated under reduced pressure. The residue crystallizes upon treatment with 200 ml of methanol. The solution is concentrated to 100 ml and left to crystallize in a refrigerator. After filtration under a vacuum and drying, dark-red 7-chloro-2-(2-methoxyacetylhydrazino)-5-(o-nitrophenyl)-3H-thieno[2,3-e]-1,4-diazepine which melts at 198°–200° C. is obtained. The product is refluxed in 400 ml of absolute xylene for 2 hours and subsequently evaporated to 150 ml under reduced pressure. After completion of the crystallization, there is obtained colorless 2-chloro-9-methoxymethyl-4-(o-nitrophenyl)-6H-thieno[3,2-f]-s-triazolo[4,3-a][1,4]diazepine which melts at 204°–205° C.

EXAMPLE 14

Unpurified 7-chloro-1,3-dihydro-5-(o-nitrophenyl)-2H-thieno[2,3-e]-1,4-diazepine-2-thione, obtained from 5 g (0.0155 mol) of 7-chloro-1,3-dihydro-5-(o-nitrophenyl)-2H-thieno[2,3-e]-1,4-diazepin-2-one, is dissolved in 500 ml of methylene chloride and refluxed for 15 hours with stirring with 15 g of sodium bicarbonate and 7 g of acetic hydrazide dimethylammonium chloride. After filtration of the solid material, the solution is washed twice with 200 ml of water each time and dried over sodium sulphate. After evaporation of the solvent, the residue is triturated with ethyl acetate, whereupon 7-chloro-2-(2-dimethylglycylhydrazino)-5-(o-nitrophenyl)-3H-thieno[2,3-e][1,4]diazepine precipitates in crystalline form. The product obtained is refluxed in 300 ml of dry butanol for 24 hours and, after evaporation of the solvent, triturated with ethyl acetate. After recrystallization from ethanol, there is obtained 2-chloro-9-dimethylaminomethyl-4-(o-nitrophenyl)-6H-thieno[3,2-f]-s-triazolo[4,3-a][1,4]diazepine as a colourless product, melting point 234°–236° C.

EXAMPLE 15

0.75 g of 2-chloro-4-(o-chlorophenyl)-6H-thieno[3,2-f]-s-triazolo[4,3-a][1,4]diazepine-9-methanol is dissolved in 25 ml of absolute chloroform and there is added thereto 0.7 g of triethylamine and 0.6 g of methanesulphochloride. The mixture is stirred for 2.5 hours at 25° C., then washed twice with water and twice with saturated sodium chloride solution, dried over sodium sulphate and evaporated. The resulting oily methanesulphonic acid ester of 2-chloro-4-(o-chlorophenyl)-6H-thieno[3,2-f]-s-triazolo[4,3-a][1,4]diazepine-9-methanol is dissolved in 10 ml of dimethylformamide and the solution added dropwise at 0°–5° C. to a solution of 1 ml of liquid ammonia in 5 ml of dimethylformamide. The mixture is stirred for 2 hours at room temperature and then partitioned between saturated sodium chloride solution and methylene chloride. The organic phase is dried and evaporated and the residue recrystallized from ethanol. There is obtained 9-aminomethyl-2-chloro-4-(o-chlorophenyl)-6H-thieno[3,2-f]-s-triazolo[4,3-a][1,4]diazepine of melting point 190°–192° C.

EXAMPLE 16

0.9 g of 2-chloro-4-(o-chlorophenyl)-6H-thieno[3,2-f]-s-triazolo[4,3-a][1,4]diazepine-9-methanol is dissolved in 20 ml of absolute chloroform and there are added thereto 0.9 g of triethylamine and 0.7 g of methanesulphochloride. The mixture is stirred for 2.5 hours at 25° C., then washed twice with water and twice with saturated sodium chloride solution, dried over sodium sulphate and evaporated. The resulting oily methanesulphonic acid ester of 2-chloro-4-(o-chlorophenyl)-6H-thieno[3,2-f]-s-triazolo[4,3-a][1,4]diazepine-9-methanol is dissolved in 10 ml of dry dimethylformamide and there is added dropwise thereto at 0°–5° C. a solution of 0.8 ml of morpholine in 5 ml of dimethylformamide. The mixture is stirred for 2 hours and then partitioned between saturated sodium chloride solution and methylene chloride. The organic phase is dried and evaporated. The residue is recrystallized from ethyl acetate containing active carbon to yield 2-chloro-4-(o-chlorophenyl)-9-morpholinomethyl-6H-thieno[3,2-f]-s-triazolo[4,3-a][1,4]diazepine, melting point 224°-226° C.

EXAMPLE 17

0.75 g of 2-chloro-4-(o-chlorophenyl)-6H-thieno[3,2-f]-s-triazolo[4,3-a][1,4]diazepine-9-methanol is dissolved in 10 ml of absolute chloroform and treated with 0.7 g of triethylamine and 0.8 g of methanesulfphochloride. The mixture is stirred for 2.5 hours at room temperature and washed twice with water and sodium chloride solution, dried over sodium sulphate and evaporated. The resulting crude methanesulphonic acid ester of 2-chloro-4-(o-chlorophenyl)-6H-thieno[3,2-f]-s-triazolo[4,3-a][1,4]diazepine-9-methanol is dissolved in 15 ml of absolute dimethylformamide and treated with 0.9 g of sodium methylmercaptide and stirred for 1 hour at 50° C. The solution is partitioned between water and methylene chloride, the organic phase is dried and evaporated. The residue is recrystallized from ethyl acetate containing active carbon. There is obtained 2-chloro-4-(o-chlorophenyl)-9-methylthiomethyl-6H-thieno[3,2-f]-s-triazolo[4,3-a][1,4]diazepine of melting point 200°-202° C.

EXAMPLE 18

1.1 g of 7-chloro-5-(o-chlorophenyl)-1,3-dihydro-2H-thieno[2,3-e]-1,4-diazepine-2-thione are refluxed for 8 hours with 1.5 g of glycolic acid hydrazide in absolute butanol. The solvent is then distilled off and the residue recrystallized from ethyl acetate containing active carbon to yield 2-chloro-4-(o-chlorophenyl)-6H-thieno[3,2-f]-s-triazolo[4,3-a][1,4]diazepine-9-methanol, melting point 219°-221° C.

EXAMPLE 19

3.27 g (0.01 mol) of 7-chloro-5-(o-chlorophenyl)-1,3-dihydro-2H-thieno[2,3-e]-1,4-diazepine-2-thione are dissolved in 200 ml of butanol and refluxed together with 5.5 g of oxalic acid ethyl ester hydrazide for 20 hours, a nitrogen stream being conducted through the solution and butanol being slowly distilled off in the first 5 hours. After evaporation of the solvent, the oil is taken up in methylene chloride, shaken out three times with 0.2-N sodium hydroxide and then three times with 0.2-N hydrochloric acid. Subsequently, the organic phase is washed with sodium bicarbonate solution, dried and evaporated. By crystallization of the residue from ethanol containing active carbon, there is obtained 2-chloro-4-(o-chlorophenyl)-6H-thieno[3,2-f]-s-triazolo[4,3-a][1,4]-diazepine-9-carboxylic acid ethyl ester, melting point 180°-182° C.

EXAMPLE 20

3.37 g (0.01 mol) of 7-chloro-1,3-dihydro-5-(o-nitrophenyl)-2H-thieno[2,3-e]-1,4-diazepine-2-thione are heated at reflux for 1 hour with 8 g of oxalic acid ethyl ester hydrazide and 150 ml of butanol, a nitrogen stream being conducted through the solution and the solvent being slowly distilled off. After completion of the evaporation of the solvent under reduced pressure, the residue is taken up in methylene chloride and shaken out, first with water, subsequently five times with 0.4-N sodium hydroxide and then twice with 0.1-N hydrochloric acid. The methylene chloride phase is shaken with dilute sodium bicarbonate solution, dried and evaporated. After complete crystallization from ethanol containing active carbon, there is obtained 2-chloro-4-(o-nitrophenyl)-6H-thieno[3,2-f]-s-triazolo[4,3-a][1,4]diazepine-9-carboxylic acid ethyl ester in the form of colorless crystals, melting point 143°-145° C.

EXAMPLE 21

1.5 g of 7-chloro-5-(o-chlorophenyl)-1,3-dihydro-2H-thieno[2,3-e]-1,4-diazepin-2-thione are refluxed for 4 hours with 4 g of 2-(p-methoxybenzyloxy)acetic acid hydrazide in 100 ml of absolute butanol, a nitrogen stream being conducted through the solution. The mixture is evaporated, taken up in methylene chloride, washed with water and saturated sodium chloride solution, dried and evaporated. By recrystallization of the residue from ethyl acetate containing active carbon, there is obtained 2-chloro-4-(o-chlorophenyl)-9-[(p-methoxybenzyloxy)methyl]-6H-thieno[3,2-f]-s-triazolo[4,3-a][1,4]diazepine.

EXAMPLE 22

A solution of 0.41 g of 2-chloro-4-(o-chlorophenyl)-6H-thieno[3,2-f]-s-triazolo[4,3-a][1,4]diazepine-9-carboxylic acid ethyl ester in 6.5 ml of absolute tetrahydrofuran is added dropwise with ice-cooling and stirring to a suspension of (0.078 g) of lithium aluminium hydride in 5 ml of absolute tetrahydrofuran. After stirring for 1 hour at 5° C., there is added dropwise 0.8 ml of 0.5-N sodium hydroxide. After filtration of the solid material, the solvent is evaporated and the residue taken up in methylene chloride. The solution is washed with 0.5-N sodium hydroxide, subsequently with water and, after drying, evaporated to dryness. By crystallization of the residue from ethyl acetate, there is obtained 2-chloro-4-(o-chlorophenyl)-6H-thieno[3,2-f]-s-triazolo[4,3-a][1,4]diazepine-9-methanol, melting point 219°-221° C.

EXAMPLE 23

0.6 g of 9-aminomethyl-2-chloro-4-(o-chlorophenyl)-6H-thieno[3,2-f]-s-triazolo[4,3-a][1,4]diazepine are dissolved in 15 ml of absolute dioxane. 1.5 g of potassium carbonate are suspended in the solution and 0.18 g of chloroformic acid ethyl ester added with stirring. After 3 hours, the solid material is filtered off from the solution. The residue obtained after evaporation of the filtrate is recrystallized from ethyl acetate containing active carbon, to yield 9-ethoxycarbonylaminomethyl-2-chloro-4-(o-chlorophenyl)-6H-thieno[3,2-f]-s-triazolo[4,3-a][1,4]diazepine.

EXAMPLE 24

1.2 g of 2-chloro-4-(o-chlorophenyl)-6H-thieno[3,2-f]-s-triazolo[4,3-a][1,4]diazepine-9-methanol are dissolved in 20 ml of absolute dioxane and warmed at 50° C. for 2 hours with 0.1 g of an 80% sodium hydride suspension. After cooling, 0.4 g of N,N-dimethylcarbonoyl chloride are added with stirring. The solution is warmed for 1 hour on a water bath and, after evaporation, partitioned between sodium bicarbonate solution and methylene chloride. The product obtained from the organic phase is recrystallized from ethanol, there being obtained 2-chloro-4-(o-chlorophenyl)-9-N,N-dimethylcarbonoyloxymethyl-6H-thieno[3,2-f]-s-triazolo[4,3-a][1,4]diazepine.

EXAMPLE 25

1 g of 2-chloro-4-(o-chlorophenyl)-6H-thieno[3,2-f]-s-triazolo[4,3-a][1,4]diazepine-9-methanol is dissolved in 10 ml of absolute pyridine and treated with 1 ml of acetic anhydride. The solution is maintained at 30° C.

for 15 hours and then evaporated under vacuum. The residue is partitioned between methylene chloride and water. The organic phase is washed with saturated sodium chloride solution, dried over sodium sulphate and evaporated. By recrystallization of the residue from ethyl acetate, there is obtained 9-acetoxymethyl-2-chloro-4-(o-chlorophenyl)-6H-thieno[3,2-f]-s-triazolo[4,3-a][1,4]-diazepine of melting point 191°–193° C.

EXAMPLE 26

0.4 g of 2-chloro-4-(o-chlorophenyl)-9-(α-hydroxyethyl)-6H-thieno[3,2-f]-s-triazolo[4,3-a][1,4]diazepine are boiled under reflux for 48 hours in 80 ml of dry toluene with 0.6 g of chromtrioxide embedded in graphite. The solid material is filtered off and the solution evaporated. The residue is recrystallized from ethanol, there being obtained 9-acetyl-2-chloro-4-(o-chlorophenyl)-6H-thieno[3,2-f]-s-triazolo[4,3-a][1,4]diazepine of melting point 89°–91° C.

EXAMPLE 27

1 g of 7-chloro-5-(o-chlorophenyl)-1,3-dihydro-2H-thieno[2,3-e]-1,4-diazepine-2-thione is refluxed for 1.5 hours in 50 ml of absolute methanol with 2 g of lactic acid hydrazide. The precipitated 7-chloro-5-(o-chlorophenyl)-2-(2-lactoylhydrazino)-3H-thieno[2,3-e]-1,4-diazepine is dried and refluxed for 4 hours in 120 ml of absolute xylene. The solution is evaporated and the product recrystallized from ethyl acetate containing active carbon to yield 2-chloro-4-(o-chlorophenyl)-9-(α-hydroxyethyl)-6H-thieno[3,2-f]-s-triazolo[4,3-a][1,4]diazepine of melting point 118°–120° C.

EXAMPLE 28

1.2 g of 7-chloro-5-(o-chlorophenyl)-1,3-dihydro-2H-thieno[2,3-e]-1,4-diazepine-2-thione are refluxed for 1.5 hours together with 2 g of cyanoacetic acid hydrazide in 80 ml of absolute methanol, a dry nitrogen stream being conducted through the solution. The solution is concentrated to 10 ml and left to crystallize. The 7-chloro-5-(o-chlorophenyl)-2-(2-cyanoacetylhydrazino)-3H-thieno[2,3-e]-1,4-diazepine, which is filtered off under a vacuum and dried, is refluxed for 2 hours in 150 ml of absolute xylene. The solution is evaporated and the residue recrystallized from ethyl acetate containing active carbon to yield 2-chloro-4-(o-chlorophenyl)-9-cyanomethyl-6H-thieno[3,2-f]-s-triazolo[4,3-a][1,4]diazepine, melting point 217°–220° C.

EXAMPLE 29

0.8 g of 7-chloro-5-(o-chlorophenyl)-1,3-dihydro-2H-thieno[2,3-e]-1,4-diazepine-2-thione are refluxed in 40 ml of absolute methanol with 1.5 g of oxalic acid amide hydrazide for 1.5 hours. The solution is concentrated to 10 ml and left to crystallize in a refrigerator. The filtered and dried 7-chloro-5-(o-chlorophenyl)-2-(2-oxalylamidohydrazino)-3H-thieno[2,3-e]-1,4-diazepine is refluxed in 100 ml of absolute xylene for 3 hours. The organic phase is evaporated and the residue recrystalized from ethanol to yield 2-chloro-4-(o-chlorophenyl)-6H-thieno[3,2-f]-s-triazolo[4,3-a][1,4]diazepine-9-carboxylic acid amide, melting point 248°–251° C.

EXAMPLE 30

0.7 g of 7-chloro-5-(o-chlorophenyl)-2-hydrazino-3H-thieno[2,3-e]-1,4-diazepine are introduced, with cooling at 15° C., into 15 ml of glacial acetic acid and a solution of 0.25 g of chloroacetyl chloride in 5 ml of glacial acetic acid is slowly added dropwise thereto. The mixture is then stirred for a further 2 hours, treated with 0.3 g of sodium acetate and stirred for 1 hour. The solution is poured on to ice-water, neutralized and shaken out with methylene chloride. After evaporation of the solvent, the residue is refluxed with 30 ml of absolute xylene for 1 hour. After evaporation of solvent, the residue is recrystallized from ethyl acetate containing active carbon to yield 2-chloro-9-chloromethyl-4-(o-chlorophenyl)-6H-thieno[3,2-f]-s-triazolo[4,3-a][1,4]diazepine, melting point 101°–103° C.

EXAMPLE 31

In a manner analogous to that described in Example 30, but using iodoacetyl iodide instead of chloroacetyl chloride, there is obtained 2-chloro-4-(o-chlorophenyl)-9-iodomethyl-6H-thieno[3,2-f]-s-triazolo[4,3-a][1,4]diazepine.

EXAMPLE 32

| Manufacture of suppositories | per suppository |
|---|---|
| 2-Chloro-4-(o-chlorophenyl)-9--methyl-6H-thieno[3,2-f]-s--triazolo[4,3-a][1,4]diazepine | 0.010 g |
| Cocoa butter (melting point 35°–37° C.) | 1.245 g |
| Carnauba wax | 0.045 g |
| Suppository weight: | 1.3 g |

The cocoa butter and carnauba wax are melted in a glass or steel vessel, thoroughly mixed and cooled to 45° C. Finely powdered 2-chloro-4-(o-chlorophenyl)-9-methyl-6H-thieno[3,2-f]-s-triazolo[4,3-a][1,4]diazepine is then added and the mixture stirred until it is completely dispersed. The mixture is poured into suppository moulds of suitable size, allowed to cool, the suppositories then removed from the moulds and packed individually in wax paper or metal foil.

EXAMPLE 33

| Manufacture of capsules | per capsule |
|---|---|
| 2-Chloro-4-(o-chlorophenyl)-9--methyl-6H-thieno[3,2-f]-s--triazolo[4,3-a][1,4]diazepine | 10 mg |
| Lactose | 165 mg |
| Maize starch | 30 mg |
| Talc | 5 mg |
| Total capsule content | 210 mg |

The 2-chloro-4-(o-chlorophenyl)-9-methyl-6H-thieno[3,2-f]-s-triazolo[4,3-a][1,4]diazepine, lactose and maize starch are first mixed in a mixer and then in a comminuting machine. The mixture is returned to the mixer, the talc added and thoroughly mixed. The mixture is mechanically filled into hard gelatine capsules.

EXAMPLE 34

| Manufacture of a parenteral formulation | per ml |
|---|---|
| 2-Chloro-4-(o-chlorophenyl)-9--methyl-6H-thieno[3,2-f]-s--triazolo[4,3-a][1,4]diazepine | 5.0 mg |
| Propyleneglycol | 0.4 ml |
| Benzyl alcohol (benzaldehyde-free) | 0.015 ml |
| Ethanol (95%) | 0.10 ml |
| Sodium benzoate | 48.8 mg |

| Manufacture of a parenteral formulation | per ml |
|---|---|
| Benzoic acid | 1.2 mg |
| Water for injection q.s. ad | 1.0 ml |

For the manufacture of 10,000 ml of an injection solution, 50 g of 2-chloro-4-(o-chlorophenyl)-9-methyl-6H-thieno[3,2-f]-s-triazolo[4,3-a][1,4]diazepine are dissolved in 150 ml of benzyl alcohol and there are added thereto 4000 ml of propyleneglycol and 1000 ml of ethanol. 12 g of benzoic acid are then dissolved in the foregoing mixture and a solution of 488 g of sodium benzoate in 300 ml of water (for injection) is added. The solution obtained is made up to a volume of 10,000 ml by the addition of water (for injection), filtered and filled into ampoules of a suitable size; the remaining volume of the ampoules is filled with nitrogen, the ampoules are heat-sealed and sterilized for 30 minutes in an autoclave at 0.7 atmospheres.

We claim:

1. A compound of the formula

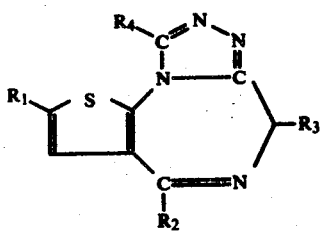

wherein $R_1$ is halogen selected from the group consisting of chlorine, bromine and iodine; $R_2$ is

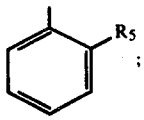

$R_3$ signifies hydrogen; $R_4$ signifies hydrogen, lower alkyl and hydroxy lower alkyl; $R_5$ signifies hydrogen, halogen, nitro or trifluoromethyl and the pharmaceutically acceptable acid addition salts thereof.

2. A compound of the formula

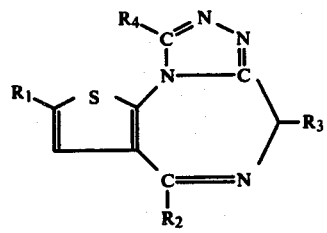

wherein $R_1$ is selected from the group consisting of chlorine, bromine, iodine, nitro, amino and lower alkanoyl; $R_2$ is

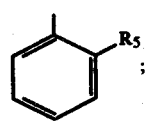

$R_3$ signifies hydrogen, hydroxy, lower alkoxy carbonyl or lower alkanoyloxy; $R_4$ signifies the group of the formula -lower alkyl-Z wherein Z signifies the grouping -N($R_7$)($R_8$) wherein $R_7$ and $R_8$ are each independently hydrogen, lower alkyl or hydroxy lower alkyl; $R_5$ signifies hydrogen, halogen, nitro or trifluoromethyl and the pharmaceutically acceptable acid addition salts thereof.

* * * * *